United States Patent [19]

Richmond et al.

[11] Patent Number: 5,144,094
[45] Date of Patent: Sep. 1, 1992

[54] DIARYL ETHERS BY DEHYDRATION OF PHENOLS

[75] Inventors: John R. Richmond, High Beach; Saad F. Tahir, London, both of England

[73] Assignee: UOP, Des Plaines, Ill.

[21] Appl. No.: 707,312

[22] Filed: Aug. 29, 1991

Related U.S. Application Data

[62] Division of Ser. No. 583,757, Sep. 17, 1990, abandoned.

[51] Int. Cl.$^5$ ............................................. C07C 41/09
[52] U.S. Cl. ................................................... 568/635
[58] Field of Search ........................................ 568/635

[56] References Cited

U.S. PATENT DOCUMENTS

| | | | |
|---|---|---|---|
| 2,487,832 | 11/1949 | Searle | 568/630 |
| 2,694,049 | 11/1954 | Reynolds et al. | 502/309 |
| 3,678,118 | 7/1972 | Frampton et al. | 502/308 X |
| 4,070,383 | 1/1978 | Rutledge | 260/396 |
| 4,360,699 | 11/1982 | Wright | 568/635 |
| 4,406,821 | 9/1983 | Farcasiu | 252/440 |
| 4,418,219 | 11/1983 | Hanes et al. | 568/697 |
| 4,487,976 | 12/1984 | Farcasiu | 568/630 |
| 4,675,454 | 6/1987 | Mossman | 568/530 |

FOREIGN PATENT DOCUMENTS

| | | | |
|---|---|---|---|
| 0196835 | 11/1984 | Japan | 568/635 |
| 72640 | 4/1988 | Japan . | |
| 1236389 | 6/1971 | United Kingdom | 568/635 |

OTHER PUBLICATIONS

Chem. Abst., 104842 (1973), Milyakh et al., "Effect of Different Factors on the Synthesis of Diphenyl Oxide".

Primary Examiner—Marianne M. Cintins
Assistant Examiner—Margaret J. Argo
Attorney, Agent, or Firm—Thomas K. McBride; Eugene I. Snyder

[57] ABSTRACT

A composite of tungsten oxide on alumina, zirconia, or titania is active in promoting the dehydration of phenols to afford diaryl ethers if the composite is partially reduced with hydrogen at a temperature between 250° and 450° C. Using such a catalyst diaryl ethers may be prepared by the dehydration of phenols in the temperature range of 350° to 550° C.

4 Claims, No Drawings

DIARYL ETHERS BY DEHYDRATION OF PHENOLS

This is a divisional of copending application(s) Ser. No. 07/583,757 filed on Sep. 17, 1990 now abandoned.

FIELD OF THE INVENTION

This invention relates to the self-condensation of phenols (dehydration) to afford diaryl ethers as the reaction product, where the reaction is catalyzed by a partially reduced tungsten oxide on a support of selected inorganic oxides.

BACKGROUND OF THE INVENTION

The class of diaryl ethers finds diverse industrial use such as multifunctional gas additives, antioxidants, heat transfer fluids, and flame retardants, to name but a few. Unfortunately, with some exceptions pertinent to unusually reactive systems, there are few commercially feasible general preparatory methods. Perhaps the most common example of diaryl ether synthesis using activated reactants is the base-catalyzed condensation of phenols with ortho- or para-nitrosubstituted halobenzenes, whose halogens are unusually susceptible to displacement, to afford the corresponding nitro-substituted diaryl ethers.

The more common methods of preparing diaryl ethers require rather severe conditions. For example, the reaction of phenols with unactivated aromatic halides, such as bromobenzene, occurs via a benzyne intermediate and this requires the use of a rather strong base, which presents increasingly unacceptable environmental problems associated with base disposal. Copper salts have been reported to catalyze this reaction (*Chem. Abst.*, 79, 104842 (1973)) but the propensity of copper salts to catalyze oxidative coupling of phenol (see, for example, U.S. Pat. No. 4,070,383) will be a complicating factor. Japanese Kokai Tokkyo Koho JP 63072640 relates to the preparation of a diphenyl ether by treating phenol or alkylated phenols with certain crystalline metal-substituted silicates, such as those of the ZSM-type. However, the self-condensation of phenol to give diphenyl ether occurs at 200° C. with only 2% conversion and 96% selectivity after 20 hours reaction time. U.S. Pat. No. 4,360,699 describes oxygen-carbon coupling between the phenolic hydroxyl and the carbon of an aromatic ring as catalyzed by aluminum at 300°-375° C. Somewhat more pertinent to the work described within is Japanese Kokai Tokkyo Koho JP 59196835 which discloses reacting a mixture of phenol, water, and benzene in the ratio of 1:0.2:3 in the gas phase over powdered titania or zirconia at 400° C. to give diphenyl ether with 67% selectivity and 42% conversion.

For various reasons the industrially preferred preparation of diphenyl ether has been the dehydration of phenol as catalyzed by thoria. The radioactivity of thoria provides an impetus for its replacement as a catalyst in an industrial process.

A good etherification catalyst should be easily compounded from readily available materials, should exhibit a good lifetime, and should not be an environmental hazard nor present environmental problems upon its disposal. We have found that if a composite of tungsten oxide supported on certain other inorganic oxides is partially reduced with hydrogen, the resulting material serves as an effective catalyst in the dehydration of phenols to give diaryl ethers. This method of preparing diaryl ethers is applicable to a diversity of phenols.

SUMMARY OF THE INVENTION

The purpose of this invention is to prepare diaryl ethers by self-condensation, or dehydration, of a phenol. An embodiment comprises reacting a phenol at a temperature between about 350° and 550° C., and preferably in the range 420°-480° C., in the presence of a catalyst which is tungsten oxide supported on alumina, zirconia, or titania in which the tungsten oxide has been partially reduced with hydrogen at a temperature between about 250° and 450° C. In a more specific embodiment the inorganic oxide is alumina. In a still more specific embodiment the catalyst is reduced at a temperature between about 350° and 400° C. Another aspect of our invention is the catalyst itself, which is a composite of tungsten (VI) oxide on alumina, zirconia, or titania where the tungsten oxide is subsequently reduced by hydrogen at a temperature in the interval of from about 250° to 450° C. Other embodiments will be apparent from the ensuing description.

DESCRIPTION OF THE INVENTION

We have observed that a catalyst resulting from partial reduction of a composite of tungsten oxide on certain inorganic oxides with hydrogen at a temperature from about 250° to 450° C. is effective in promoting the dehydration of phenols in the temperature range of about 350° to 550° C. to afford diaryl ethers. Farcasiu in U.S. Pat. No. 4,406,821 and 4,487,976 has described a sulfated composite of oxides of transition metals, including tungsten, on an alumina support to etherify phenols with aliphatic alcohols or aliphatic ethers, but the patentee has not disclosed the use of his catalyst in dehydration of phenols. In fact, we have found that the patentee's catalyst is completely inactive in preparing diphenyl ether by dehydration of phenol.

The efficacy, and even the operability, of the catalysts of our invention are sensitive to the nature of the support on which tungsten oxide is deposited. We have found that inorganic oxides, principally alumina, zirconia, and titania, are especially effective supports. Among these alumina appears to be the support of choice because of its availability and convenience in use.

The next stage in catalyst preparation is deposition of tungsten (VI) oxide on the support. Deposition of tungsten (VI) oxide on a support is well known to practitioners of catalyst art and will not be described in great detail. The two methods described below are but representative of those which may be used in the successful practice of our invention.

One method of effecting the deposit of tungsten oxide on a support is by impregnating a support with a solution of an appropriate tungsten compound, which is essentially a pore-filling method. Ammonium tungstate solutions are particularly convenient to use, and after impregnation excess water may be removed by decantation followed by drying of the impregnated support at temperatures somewhat greater than 100° C. with subsequent calcination at temperatures on the order of 300°-500° C. Multiple impregnations can be used to obtain higher levels of tungsten oxide deposits. That is, after an initial impregnation with, for example, an ammonium tungstate solution the calcined material may be reimpregnated with additional ammonium tungstate solution to increase the amount of tungsten oxide deposited on the support.

A deposite of tungsten oxide on the support also may be prepared by a co-mixing technique, which involves continuous addition of a tungsten salt solution to the support with concurrent mixing and heating to evaporate water. For example, a solution of a suitable ammonium tungstate, such as ammonium tungstate dissolved in 5% oxalic acid solution, can be added to the support with continuous mixing. The resulting product can then be subsequently air dried and the dried product can be mixed with additional solution until the desired amount of tungsten is deposited on the support. The resulting product can then be dried at temperatures somewhat above 100° C. followed by calcination at 350°-500° C. The co-mixing technique is capable of affording very high concentrations of tungsten oxide on the support, up to perhaps as high as 70 weight percent tungsten oxide based on total composite.

As can be expected, the activity of our catalysts generally increases with increasing tungsten oxide concentration. A practical lower limit of 3 weight percent tungsten oxide, based on total composite arises from activity considerations. No upper limit exists; loadings of at least about 50 weight percent tungsten oxide may be achieved, although at very high loadings the tungsten oxide may be inefficiently utilized. As a practical matter composites containing from about 5 through about 20 weight percent tungsten oxide generally will be chosen.

The composite prepared as described up to this point is inactive as a catalyst in promoting the dehydration of phenols to form diaryl ethers. An essential prerequisite for catalytic properties is prior partial reduction of the tungsten on the composite with hydrogen. The most convenient method is to reduce the composite with a stream of hydrogen diluted in an inert gas such as nitrogen or argon. Gas mixtures containing from about 3 to about 20 volume percent hydrogen, and more preferably between 5 and 10 volume percent hydrogen, are favored in the partial reduction of tungsten oxide. Reduction temperatures are in the range from about 250° to about 450° C., more commonly between 350° and 400° C. Reduction time depends on such factors as sample size, the apparatus used, flow rate, mixing efficiency, and so on. However, when in situ reduction is performed in a fixed bed reduction times of about 1 hour are feasible.

The nature of the tungsten species in the catalyst is not known with certainty. Without wishing to be bound by any theory, our working hypothesis is that under the conditions of reduction employed tungsten is largely converted to tungsten (IV), which has an electronic configuration similar to that of thorium in thoria, also an active dehydration catalyst.

Phenols generally may be used in the practice of this invention. By "phenol" is meant any aromatic compound having an hydroxyl group directly attached to the aromatic nucleus. As to specific phenols, after phenol itself alkyl phenols are perhaps the most important class of phenols used in my invention, especially lower alkyl phenols where the alkyl groups contain up to about 8 carbon atoms, and more particularly alkyl groups containing up to about 4 carbon atoms. Examples include the methyl phenols, commonly known as cresols, ethyl phenol, propyl phenol, butyl phenol, pentyl phenol, hexyl phenol, octyl phenol, dimethyl phenol, diethyl phenol, dipropyl phenol, dibutyl phenol, methylethyl phenol, and so on. Halogen-substituted phenols also may be successfully used in the practice of my invention, especially when the halogen is chlorine or bromine. Alkoxy substituted phenols, especially where the alkoxy group contains no more than 4 carbon atoms, is another class of phenols which may be commonly used in the practice of my invention.

The self-condensation of phenols to afford diaryl ethers may be run in either a batch or continuous method of operation. It is perhaps most convenient to carry out the reaction continuously where the catalyst is employed as a fixed bed. Typically, the phenol, or a solution of the phenol in an inert solvent, will be fed downflow over the fixed bed of the catalysts of our invention. Although the phenol may be diluted with a solvent such a variant generally has no advantage in the practice of our invention. The fixed bed typically is maintained at a temperature between about 350° and 550° C., and the liquid hourly space velocity is adjusted to optimize the reaction. Effluent is collected, and, where desired, the diaryl ether is separated from the reactants and from products other than the desired diaryl ether.

The following examples are only illustrative of our invention and are not intended to limit its scope in any way.

EXAMPLE 1

General Testing Procedure

This illustrates the procedure for testing the catalytic activity of various materials in the dehydration of phenol to diphenyl ether. About 1 mL (0.3–1.1 gm, 20–30 mesh, bed length about 6 cm) of the putative catalyst was packed into a microreactor (stainless steel tubing 4.5 mm O.D.×105 mm having a wall thickness of 0.8 mm) connected to a GC oven/column. The putative catalyst was reduced in situ with a 5% $H_2/N_2$ gas mixture at 350° C. for 1 hr, then was cooled under pure $N_2$ gas which is used as carrier gas. A solution of phenol in benzene (1:1) molar ratio was injected over the putative catalyst at different reaction temperatures in the interval 350°–520° C. The temperature in the catalyst bed was measured by means of a thermocouple inserted into the middle of the catalyst bed.

The gas mixture after the reaction was analyzed using a F-11 Perkin Elmer chromatograph using 2 m×⅛" OV-17 (4%) on 100–120 mesh chromosorb W/AW with a flame ionization detector. The flow rate of the carrier gas ($N_2$) was 55 mL/min. The separation of the products and unreacted reactant was carried out at an initial oven temperature of 100° C.; after appearance of the benzene peak, the temperature was increased 10° C./min. to 180° C. to obtain a good separation for phenol and diphenyl ether. The injection rate of the feed stock phenol-benzene solution was about 1 μl/20 min.

EXAMPLE 2

Catalyst Preparation

Part A

A composite 6.3 weight percent tungsten oxide supported on gamma alumina catalyst was prepared by impregnation in the following manner. Ammonium tungstate solution (1.6 gram ammonium tungstate in 75 ml hot water) was added to gamma alumina (20 gm, surface area 154 $m^2g^{-1}$, 20–30 mesh) and after 20 minutes excess water was evaporated. The impregnated alumina was dried for 4 hours at 110° C., then calcined in air for 4 hours at 450° C., to afford a 6.3 weight percent tungsten oxide loading. Sequential re-impregnation was employed to give higher tungsten oxide loading based on the total composite weight. Catalysts can be prepared from composites by reduction with 3-20% hydrogen (diluted with argon or nitrogen) at 250°–450° C., although conditions described in Example 1 were generally employed.

A series of catalysts with loading of 6.3 weight percent (based on total composite) tungsten oxide on other supports was prepared, namely activated carbon (609 $m^2g^{-1}$), $Fe_2O_3$ (56 $m^2g^{-1}$), MgO (42 $m^2g^{-1}$), molecular sieve ZSM-5 (498 $m^2g^{-1}$), $SnO_2$ (137 $m^2g^{-1}$), $SiO_2$ (57 $m^2g^{-1}$), $TiO_2$ (anatase, 60 $m^2g^{-1}$), $ZrO_2$ (44 $m^2g^{-1}$) and $ZrO_2$ (Degussa, 70 $m^2g^{-1}$) by impregnating only once with ammonium tungstate solution, drying and then calcining in air at 450° C. The tungsten oxide catalyst supported on activated carbon was calcined under $N_2$ atmosphere.

Part B

A 46.8 weight percent tungsten oxide supported on gamma alumina was prepared by a co-mixing technique in the following manner. Ammonium tungstate (190 gram) was dissolved in 2 liters of warm aqueous 5% oxalic acid solution. This solution (50 ml) was added to the gamma alumina (200 gram) with continuous mixing. The product was dried at 110° C. in air and the addition of 50 ml of the solution with stirring was repeated until all the solution was deposited on the alumina support. The catalyst was then dried at 110° C. for 4 hours followed by calcination in air for 4 hours at 450° C.

EXAMPLE 3

Tungsten Oxide on Alumina Catalyst I

A 6.3 weight percent tungsten oxide/alumina catalyst (0.24 gm, 1 cc) was prepared by impregnation, reduced in situ, and tested in the microreactor as in Example 1 at reaction temperatures of 369°–475° C. The results, reported in Table 1, were obtained after reaching steady state conditions by exposure of the catalyst to the equivalent of about 134 μl phenol:benzene ratio (1:1). A similar experiment carried out without hydrogen pretreatment of the composite showed no activity of unreduced composite for diphenyl ether formation at reaction temperatures of 390°–510° C.

TABLE 1

| Temperature °C. | Conversion % Phenol | Selectivity % Diphenyl ether | Selectivity % 4-Phenyl phenol | Selectivity % Dibenzofuran |
|---|---|---|---|---|
| 369 | 63.9 | 8.4 | 1.1 | 3.5 |
| 381 | 65.2 | 6.7 | 0.5 | 3.1 |
| 396 | 65.1 | 11.4 | — | 3.4 |
| 408 | 62.0 | 12.0 | 0.6 | 2.7 |
| 413 | 67.0 | 11.0 | 0.8 | 4.0 |
| 423 | 68.4 | 11.6 | 0.4 | 4.8 |
| 444 | 69.1 | 11.3 | 0.2 | 6.6 |
| 459 | 71.1 | 11.4 | 0.8 | 5.6 |
| 475 | 70.9 | 11.4 | 0.7 | 5.1 |

EXAMPLE 4

Tungsten Oxide on Alumina Catalyst II

A 46.8 weight percent tungsten oxide/alumina composite (0.57 gm, 1 cc) was prepared by co-mixing, reduced in situ, and tested in the microreactor as in Example 1 at reaction temperatures between 404°–480° C. The results are reported in Table 2 after exposure of the catalyst to the equivalent of about 169 μl of phenol:benzene ratio (1:1).

TABLE 2

| Temperature °C. | Conversion % Phenol | Selectivity % Diphenyl ether | Selectivity % 4-Phenyl phenol | Selectivity % Dibenzofuran |
|---|---|---|---|---|
| 404 | 66.7 | 16.6 | — | 4.8 |
| 420 | 64.1 | 18.2 | 0.5 | 3.3 |
| 435 | 66.4 | 16.6 | 0.8 | 5.4 |
| 451 | 67.6 | 22.3 | 0.8 | 0.6 |
| 465 | 70.8 | 24.8 | 0.6 | 1.3 |
| 480 | 73.3 | 20.6 | — | 1.6 |

EXAMPLE 5

Tungsten Oxide on Titania

A 6.3 weight percent tungsten oxide/titania (anatase) catalyst (0.37 gm, 1 cc) prepared as described above for the tungsten oxide/alumina catalyst of Example 3 was tested in the microreactor as in Example 1 over the temperature range of 415°–520° C. The results are reported in Table 3 after exposure of the catalyst to the equivalent of about 140 μl of phenol:benzene ratio (1:1).

TABLE 3

| Temperature °C. | Conversion % Phenol | Selectivity % Diphenyl ether | Selectivity % 4-Phenyl phenol | Selectivity % Dibenzofuran |
|---|---|---|---|---|
| 415 | 74.3 | 3.8 | 16.0 | 0.4 |
| 431 | 77.6 | 2.7 | 15.6 | 0.4 |
| 445 | 86.3 | 2.6 | 11.9 | 7.4 |
| 460 | 84.6 | 4.6 | 12.0 | 3.4 |
| 475 | 95.1 | 7.6 | 13.7 | 12.1 |
| 490 | 93.0 | 9.0 | 11.6 | 13.3 |
| 505 | 96.8 | 12.5 | 11.5 | 9.1 |
| 520 | 96.7 | 12.1 | 12.6 | 14.3 |

EXAMPLE 6

Tungsten Oxide on Zirconia

A 6.3 weight percent tungsten oxide/zirconia catalyst (0.56 gm, 1 cc) was tested as in Example 1 at 404°–505° C. The results are reported in Table 4 after exposure of the catalyst to the equivalent of about 130 μl of phenol:benzene ratio (1:1).

TABLE 4

| Temperature °C. | Conversion % Phenol | Selectivity % Diphenyl ether | Selectivity % 4-Phenyl phenol | Selectivity % Dibenzofuran |
|---|---|---|---|---|
| 404 | 83.5 | 7.2 | 2.0 | 6.3 |
| 419 | 87.3 | 8.9 | 9.3 | 7.1 |
| 453 | 90.3 | 9.6 | 7.0 | 7.6 |
| 468 | 88.4 | 8.9 | 9.2 | 5.2 |
| 484 | 89.2 | 7.2 | 11.2 | 7.1 |
| 498 | 90.5 | 4.1 | 10.3 | 9.2 |
| 505 | 91.8 | 3.1 | 5.8 | 7.1 |

EXAMPLE 7

Effect of Supports on Catalytic Activity

A series of materials containing 6.3 weight percent tungsten oxide on different supports as well as several blank supports (1 cc) were tested for catalytic activity under experimental conditions similar to those described in Example 1. None of the materials in this example, summarized in Table 5, showed activity for diphenyl ether over the temperature range tested.

TABLE 5

Inactive Supports

| Material | Wt. of Sample (GM) | Reaction Temperature Range/°C. |
|---|---|---|
| Tungsten oxide/silica | 0.38 | 440–509 |
| Tungsten oxide/tin oxide | 1.4 | 380–492 |
| Tungsten oxide/iron oxide | 1.0 | 350–500 |
| Tungsten oxide/ZSM-5 | 0.42 | 386–483 |
| Tungsten oxide/carbon | 0.2 | 387–480 |
| Tungsten oxide/magnesia | 0.4 | 434–527 |
| Tungsten oxide/zirconia (Degussa) | 0.6 | 400–500 |
| Alumina[1] | 0.26 | 350–500 |
| Tungsten oxide/alumina[2] | 0.28 | 350–470 |
| Alumina[2] | 0.25 | 390–510 |
| Titania (anatase)[2] | 0.4 | 440–510 |
| Zirconia[2] | 0.75 | 400–500 |

[1] The support was pretreated with hydrogen as if tungsten oxide were present.
[2] The experiment was carried out without any hydrogen pretreatment of the catalyst or support.

EXAMPLE 8

Tungsten Oxide on Alumina using p-Cresol

A 46.8 weight percent tungsten oxide/alumina catalyst (0.43 gm, 1 cc) was prepared by co-mixing and reduction in situ, then tested in the microreactor as in Example 1 using a p-cresol:benzene mixture with molar ratio 1:1 in the temperature range of 433°–472° C. The results are reported in Table 6.

TABLE 6

| Temperature °C. | Conversion % Cresol | Yield % Ditolyl ether | Selectivity % Ditolyl ether |
|---|---|---|---|
| 433 | 96.5 | 5.0 | 5.2 |
| 442 | 98.1 | 3.3 | 3.4 |
| 462 | 96.2 | 6.5 | 6.8 |
| 472 | 98.6 | 2.9 | 2.9 |

What is claimed is:

1. A method of making diaryl ethers comprising dehydrating a phenol at a temperature from about 350° to about 550° C. in the presence of a catalyst comprising a composite resulting from the reduction of tungsten (VI) oxide deposited on a refractory inorganic oxide selected from the group consisting of alumina, zirconia, and titania, said composite having been reduced with hydrogen at a temperature between about 250° and about 450° C. for a time effective to partially reduce the tungsten (VI) oxide, and recovering the resulting diaryl ether.

2. The method of claim 1 where the phenol is phenol or a cresol.

3. The method of claim 2 where the phenol is phenol.

4. The method of claim 1 where the reaction is conducted at a temperature between about 420° to about 480° C.

* * * * *